United States Patent [19]
Dieterich et al.

[11] 4,359,426
[45] Nov. 16, 1982

[54] PROCESS FOR THE PRODUCTION OF AROMATIC ISOCYANATES CONTAINING AROMATICALLY BOUND SULFOCHLORIDE GROUPS

[75] Inventors: Dieter Dieterich, Leverkusen; Heinz U. Blank, Odenthal; Erich Wolters, Niederzier; Norbert Langenfeld, Cologne, all of Fed. Rep. of Germany

[73] Assignee: Bayer Aktiengesellschaft, Leverkusen, Fed. Rep. of Germany

[21] Appl. No.: 230,193

[22] Filed: Feb. 2, 1981

[30] Foreign Application Priority Data

Feb. 8, 1980 [DE] Fed. Rep. of Germany ....... 3004694

[51] Int. Cl.$^3$ .......................................... C07C 119/048
[52] U.S. Cl. ...................... 260/453 AR; 260/453 AM
[58] Field of Search ................ 260/453 AR, 453 AM, 260/543 R

[56] References Cited

U.S. PATENT DOCUMENTS 3,686,301  8/1972  Kirch ............................ 260/544 M

FOREIGN PATENT DOCUMENTS 574836  3/1933  Fed. Rep. of Germany .
947159  8/1956  Fed. Rep. of Germany .

OTHER PUBLICATIONS

Houben-Weyl, 4th Edition, vol. 9, pp. 563-585.

Primary Examiner—Dolph H. Torrence
Attorney, Agent, or Firm—Gene Harsh; Joseph C. Gil; Richard A. Elder

[57] ABSTRACT

The instant invention is directed to a process for the production of an aromatic isocyanate containing aromatically bound sulfochloride groups, comprising:
(I) reacting
  (a) an isocyanate or carbamic acid chloride which contains at least one aromatically bound isocyanate group and/or at least one aromatically bound carbamic acid chloride group, successively or simultaneously at 0° to 170° C. with
  (b) a sulfonating agent and
  (c) an organic compound containing at least one aromatically bound trihalo methyl group and
(II) removing hydrogen chloride from the reaction mixture at 20° to 170° C.

5 Claims, No Drawings

PROCESS FOR THE PRODUCTION OF AROMATIC ISOCYANATES CONTAINING AROMATICALLY BOUND SULFOCHLORIDE GROUPS

BACKGROUND OF THE INVENTION

Isocyanato-aryl sulfochlorides are known. According to German Pat. No. 947,159 they may be obtained by phosgenating aromatic aminosulfonic acids. The disadvantage of this process lies in the need to use high-boiling solvents, such as dichlorobenzene and, in particular, nitrobenzene. Another disadvantage is the poor solubility of the aminosulfonic acids used as starting material in these solvents, even at the high reaction temperatures applied. As a result, the reaction is laborious and the yield of the isocyanato-aryl sulfochlorides obtained is unsatisfactory. This applies in particular to the production of diisocyanato-aryl sulfochlorides. In Example 3 of German Pat. No. 947,159, for example, a yield of 46% of the theoretical was obtained. Because of the disadvantages referred to above, this process has not acquired any commercial significance.

It is also known that simple aryl sulfochlorides can be obtained by sulfonating aromatic compounds, for example, with chlorosulfonic acid or with mixtures of chlorosulfonic acid and sulfuryl chloride (cf. for example, Houben-Weyl, 4th Edition, Vol. 9, pages 563 to 585). It is also known that sulfochlorides can be produced from free sulfonic acids or their salts with acid chlorides. Prior to the instant invention, these known processes have rarely been used for the manufacture of isocyanato-aryl sulfochlorides from aromatic isocyanates, and only with negative results, there are several reasons for this.

First, the sulfochlorination reaction with chlorosulfonic acid requires an excess of chlorosulfonic acid and hence, necessitates working-up in the presence of water with the result that the isocyanate groups are attacked. Second, isocyanato-sulfonic acids in the form of dimeric uretdiones have only recently become known and have proved to be extremely reactive compounds which are very difficult to handle. In addition, sulfonic acid groups react unpredictably with isocyanates at elevated temperature, with the elimination of carbon dioxide. Thus, under the conditions normally used for the production of sulfochlorides, other reactions, for example, sulfone and anhydride forming reactions and also polymerization reactions involving the isocyanate group, can be expected to take place to a considerable extent.

It is known from U.S. Pat. No. 3,686,301 that 3,5-dichlorosulfobenzoyl chloride can be obtained by reacting 3,5-disulfobenzoic acid heated to 180° C. with 3 times the molar quantity of benzotrichloride. The benzotrichloride is added over a period of 3 hours and the temperature is slowly reduced to 130° C. during the addition and the mixture is stirred for another hour at 130° C.

It is also known (cf. German Pat. No. 574,836) that the sodium salts of aromatic sulfonic acids can be reacted with benzotrichloride to form the corresponding aromatic sulfonic acid chloride. In addition, according to this German patent, the known reaction of free carboxylic acids with benzotrichloride in the presence of zinc chloride for producing the carboxylic acid chlorides cannot be applied to free organic sulfonic acids.

Prior to the instant invention, it was unknown to react isocyanato-aryl sulfonic acid uretdiones with aromatic trihalogen methyl compounds. The misgivings expressed above also apply to this reaction, especially since it is carried out at temperatures above 100° C.

It has now surprisingly been found that compounds containing aromatically bound isocyanate groups or aromatically bound carbamic acid chloride groups can also be converted particularly easily in good yields into aromatic isocyanates containing aromatically bound sulfochloride groups, providing that the starting materials are reacted successively or simultaneously with sulfonating agents and compounds containing aromatically bound trihalogen methyl groups. The expected complex secondary reactions which generally occur because of the presence of highly reactive isocyanate groups or carbamic acid chloride groups do not result. In addition, the use of the above-mentioned aromatic trihalogen methyl compounds has the advantage over the use of thionyl chloride or phosgene as the halogenating agent that no acid amide is used as catalyst. Also, in the case of low molecular weight process products, the crude product may be distilled directly without preliminary purification.

DESCRIPTION OF THE INVENTION

The present invention relates to a process for the production of an aromatic isocyanate containing aromatically bound sulfochloride groups, comprising:

(I) reacting
 (a) an isocyanate or carbamic chloride which contains at least one aromatically bound isocyanate group and/or at least one aromatically bound carbamic acid chloride group, successively or simultaneously at 0° to 170° C. with
 (b) a sulfonating agent and
 (c) an organic compound containing at least one aromatically bound trihalogen methyl group and
(II) removing hydrogen chloride from the reaction mixture at 20° to 170° C.

Suitable starting materials (a) for the process according to the invention are any organic compounds which contain at least one isocyanate group bound to an aromatic ring and/or at least one carbamic acid group bound to an aromatic ring and which, apart from their ability to be sulfonated, are otherwise inert under the reaction conditions of the process according to the invention.

Particularly suitable starting materials (a) are, for example, phenyl isocyanate; p-tolyl isocyanate; m-tolyl isocyanate; p-chlorophenyl isocyanate; m-chlorophenyl isocyanate; p-bromophenyl isocyanate; p-methoxyphenyl isocyanate; p-ethoxy phenyl isocyanate; p-trifluoromethyl phenyl isocyanate; m-trifluoromethyl phenyl isocyanate; 2,4-diisocyanatotoluene or mixtures thereof with up to 35% by weight, based on the mixture as a whole, of 2,6-diisocyanatotoluene; 2,2'-diisocyanatodiphenyl methane; 2,4'-diisocyanatodiphenyl methane; 4,4'-diisocyanatodiphenyl methane; mixtures of these isomers and commercial polyphenyl polymethylene polyisocyanates of the type obtained by condensing aniline with formaldehyde, followed by phosgenation, described for example in British Pat. Nos. 874,430 and 848,671.

Instead of using the diisocyanates and polyisocyanates mentioned by way of example above, it is also possible to use their modification products containing isocyanate groups and allophanate, biuret, urethane, urea, carbodiimide, isocyanurate or acyl urea groups.

They may be obtained by a modification reaction of some of the isocyanate groups of the diisocyanates or polyisocyanates. It is also possible to use distillation residues containing isocyanate groups of the type encountered in the commercial production of aromatic diisocyanates and polyisocyanates, optionally in solution in one or more of the above-mentioned polyisocyanates. Mixtures of the above-mentioned compounds containing isocyanate groups may also be used.

Instead of using the starting compounds (a) containing isocyanate groups mentioned by way of example, it is also possible to use for example the corresponding carbamic acid chlorides containing aromatically bound carbamic acid chloride groups as component (a). "Corresponding carbamic acid chlorides" are understood to be compounds containing carbamic acid chloride groups of the type which may be obtained, for example, by the addition of hydrogen chloride with the isocyanate groups of the above isocyanates or the intermediate products formed during the phosgenation of amines to produce the above isocyanates.

In the process according to the invention, any sulfonating agents for aromatic compounds may be used as starting component (b). Particularly suitable sulfonating agents are sulfur trioxide and/or chlorosulfonic acid. The sulfur trioxide may be used in liquid, dissolved or gaseous form, for example, in nitrogen-diluted form, or in the form of an addition compound with organic compounds. Such addition compounds include the adducts of sulfur trioxide with dioxane, tetrahydrofuran, diethyl ether or dimethyl formamide. It is preferred to use gaseous sulfur trioxide. Any solvents used for the sulfur trioxide must be inert to sulfur trioxide and also to isocyanate groups under the reaction conditions of the process according to the invention. Suitable solvents are, for example, halogenated or nitrated hydrocarbons such as, for example, dichloroethane, tetrachloroethane, methylene chloride, chloroform, fluorotrichloromethane, nitromethane, nitrobenzene, diethyl ether, dioxane, tetrahydrofuran, sulfur dioxide, chlorobenzene, dichlorobenzene or, preferably, excess quantities of the trihalogen methyl compounds mentioned hereinafter.

Any organic compounds which contain at least one trihalogen methyl substituent and which are inert in particular to isocyanate groups and carbamic acid chloride groups may be used as component (c).

In this context "trihalogen methyl groups" are primarily understood to be tribromomethyl or trichloromethyl groups, preferably trichloromethyl groups. Particularly suitable are benzotribromide or benzotrichloride which may contain substituents which are inert under the reaction conditions of the process according to the invention, benzotrichloride and its derivatives containing inert substituents being particularly preferred.

Typical representatives of suitable starting components (c) are, for example, compounds corresponding to the following formula

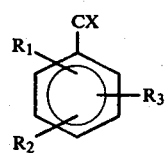

in which $R_1$, $R_2$ and $R_3$ are the same or different and represent hydrogen, $C_1$–$C_6$-alkyl, $C_5$–$C_7$-cycloalkyl, $C_6$–$C_{10}$-aryl, $C_7$–$C_{10}$-aralkyl, $C_1$–$C_4$-alkoxy, $C_6$–$C_{10}$-aroxy, $CX_3$, chlorine or bromine radicals or radicals corresponding to the following formulae

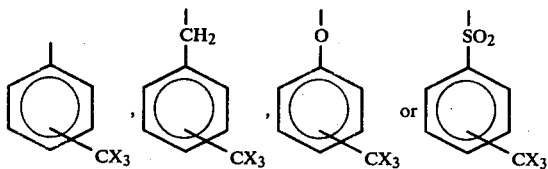

or two of the radicals $R_1$ to $R_3$, when they are adjacent, may form part of a condensed cycloaliphatic or aromatic ring which may be substituted by $CX_3$-groups, and X represents chlorine or bromine.

Particularly preferred starting components (c) are those corresponding to the first general formula in which $R_1$, $R_2$ and $R_3$ represent hydrogen or in which one of the radicals represents a $C_1$–$C_2$-alkyl group and X is as defined above, but preferably represents chlorine.

Typical representatives of suitable reaction components (c) are, for example, the following compounds: benzotrichloride, 1-chloro-2-trichloromethyl benzene, 1-chloro-4-trichloromethyl benzene, 2,4-dichloro-1-trichloromethyl benzene, 1,3-bis-(trichloromethyl)-benzene, 1,4-bis-(trichloromethyl)-benzene, 1-trichloromethyl naphthalene, 2-trichloromethyl naphthalene, 4-trichloromethyl biphenyl, 4,4'-bis-(trichloromethyl)-biphenyl, 4-trichloromethyl diphenyl ether, 4-trichloromethyl diphenyl methane, benzotribromide, 1-bromo-2-tribromomethyl benzene and 1-bromo-4-tribromomethyl benzene.

The process according to the invention is preferably carried out in the absence of catalysts. However, it is also possible catalytically to accelerate the halogenation reaction using component (c), suitable catalysts being Broensted acids or Lewis acids. Suitable Broensted acids are, for example, sulfuric acid, pyrosulfuric acid, phosphoric acid, pyrophosphoric acid and the acid salts of these acids. Also, polyphosphoric acid, fluorosulfonic acid, chlorosulfonic acid and bromosulfonic acid may be used. Lewis acids suitable for the process according to the invention are, for example, thionyl chloride, sulfuryl chloride, phosphorus pentoxide, phosphorus trichloride, phosphorus oxychloride, aluminum chloride, iron dichloride, iron trichloride, zinc chloride, boron trifluoride, boron trichloride or tin tetrachloride. The Broensted acids and Lewis acids mentioned above may be used individually, in the form of a mixture of different Broensted acids, in the form of a mixture of different Lewis acids or in the form of a mixture of Broensted and Lewis acids.

The Broensted or Lewis acid is used, if at all, in a quantity of, for example, from 0.01 to 3 mole percent and preferably in a quantity of from 0.1 to 2 mole percent, based on the isocyanate or carbamic acid chloride used.

In general, from 0.2 to 2 moles of (a) sulfonating agent are used per mole of (b) isocyanate or carbamic acid chloride. A molar ratio of (a) to (b) of from 1:0.4 to 1:1.5 is particularly preferred. In the production of the defined monosulfonic acid chlorides, a molar ratio of (a) to (b) of from 1:1 to 1:1.2 is generally maintained. Where it is desired to introduce two sulfochloride groups into one molecule of starting component (a), a molar ratio of (a) to (b) from 1:1.8 to 1:2 is used. Basically, it is important to ensure that the sulfonating agent used is largely consumed during the reaction with the diisocyanate or that any excess used is removed, so that no excess of sulfonating agent is present on completion of the sulfonation reaction. On the other hand, it is entirely possible to effect only partial sulfochlorination of component (a) by using less than the equivalent quantity of the above-mentioned sulfonating agent. For example, it is possible to use a molar ratio of from 1:0.2 to 1:0.9.

The organic compound containing at least one aromatically bound trihalo methyl group (c) is used in at least an equivalent quantity to component (b). In general, it is used in 1.5 to 10 times the molar quantity, based on component (b). Accordingly, the molar ratio of (a) to (c) is from 1:0.2 and 1:20 and preferably from 1:0.3 to 1:20. Where components (a) and (b) are used in equimolar quantities, as is particularly preferred, component (c) is preferably used in 1.5 to 8 times the molar quantity, based on component (a). Although not critical to the process according to the invention, the use of more than 10 times the molar quantity of component (c), based on component (b), is less favorable on economic grounds. The excess of component (c) serves as solvent in the process according to the invention.

In the reaction according to the invention, the corresponding acid halides are formed from trihalogen methyl compounds, so that these acid halides (for example, benzoic acid chloride from benzotrichloride) may be regarded as secondary products of the process according to the invention. On the other hand, it is particularly these acid chlorides corresponding to component (c) which are also very suitable for use as solvent for the halogenation reaction according to the invention. Other solvents which may be used in accordance with the invention are, for example, dichloroethane, tetrachloroethane, nitromethane, nitrobenzene, chlorobenzene and o-dichlorobenzene.

The simultaneous or successive reaction of component (a) with components (b) and (c) according to the invention is generally carried out at temperatures in the range from 0° to 170° C. The reaction according to the invention with component (c), which may be carried out at the same time as or after the sulfonation reaction, is preferably carried out at temperatures in the range from 10° C. to 150° C. and, with particular preference, at temperatures in the range from 20° to 140° C. Where the reaction according to the invention is carried out in two stages, as is preferably the case, the sulfonation reaction is preferably carried out at temperatures in the range from 0° to 80° C. and, more particularly, at temperatures in the range from 0° to 40° C. in the first stage, followed by the halogenation reaction at temperatures within the ranges mentioned above.

The process according to the invention may be carried out in several different ways:

1. The sulfonating agent (b) is initially added to component (a), followed by the addition of component (c) on completion of the sulfonation reaction. In this case, the uretdiones of the corresponding isocyanato-aryl sulfonic acids, solid insoluble compounds, are formed as intermediate. In order to guarantee stirrability, the sulfonation reaction has to be carried out either in the presence of one of the above-mentioned solvents inert in particular to sulfonating agents and/or in the presence of an excess of component (a). If the molar ratio of (a) to (b) is between 1:0.7 and 1:2, the use of a solvent is unavoidable. After the sulfonation reaction, the solvent used or the excess starting isocyanate (a) may be completely or even partly removed, for example, by filtration under suction, centrifuging or even distillation. Before the second stage of the reaction, the sulfonating agent should either be consumed or, where an excess of component (b) is used, should be removed from the reaction mixture, for example, by washing out with an inert solvent or even by distillation. In this case, the sulfonating agent may even be used in a quantity exceeding the above-mentioned molar ratio (a):(b) of 1:2.

With a molar ratio of (a) to (b) of from 1:1.5 to 1:2, the order in which the starting components (a) and (b) are combined is not critical. Thus, it is possible, for example, to add the sulfonating agent to component (a), optionally dissolved in an inert solvent, or to introduce component (a) into a solution of the sulfonating agent (b) in such a solvent. Where the molar ratio (a):(b) is between 1:0.2 and 1:1.49, the sulfonating agent should be added to component (a) beforehand.

In this first embodiment, the second stage of the process according to the invention is carried out on completion of the sulfonation reaction by mixing the sulfonation product with component (c). After this mixing step, the reaction mixture is kept within the above-mentioned temperature ranges until no more hydrogen halide escapes.

2. In a second possible embodiment of the process according to the invention, component (a) is initially mixed with component (c), followed by addition of the sulfonating agent (b). In this case in particular, component (c) may simultaneously perform the function of a solvent. The reaction mixture is then kept within the above-mentioned temperature ranges until the formation of hydrogen halide has ceased.

3. In a third embodiment of the process according to the invention, the sulfonating agent (b) and component (c) are allowed to act simultaneously on component (a). For example, component (a) may be treated with a solution of chlorosulfonic acid in benzotrichloride. In this embodiment, it is of particular advantage to add the mixture of components (b) and (c) to component (a) at around 0° to 20° C. and then gradually to increase the temperature to around 140° C. In this case, too, the reaction is continued until no more hydrogen halide escapes from the reaction mixture.

In all three embodiments of the process according to the invention, the hydrogen chloride is then removed as completely as possible, for example, by heat treatment at 20° to 170° C. and preferably at 80° to 170° C.

The first embodiment of a two-stage reaction is preferred to the single-stage reaction of embodiments 2 or 3.

On completion of the reaction according to the invention, the solvents used, if any, the carboxylic acid chloride formed and excess component (c) are removed, preferably by distillation. The liquid distillation residue contains the process product and is sufficiently pure for many applications.

Where the process product consists of defined sulfochlorides, crystallization frequently occurs during cooling of the distillation residue. In that case, the products of the process may be purified by recrystallization.

One particular advantage of the process according to the invention is that, in most cases, the crude product may be purified by distillation without any need for preliminary purification.

The process according to the invention is particularly suitable for the production of 2,4-diisocyanatotoluene-5-sulfochloride; an isomer mixture predominantly containing 2,4-diisocyanatotoluene-5-sulfochloride; 2,4-diisocyanatotoluene-3,5-disulfochloride or isomers or homolog mixtures which, in addition to the disulfochloride mentioned, contain 2,4-diisocyanatotoluene-5-sulfochloride and 2,4-diisocyanatotoluene-5-sulfochloride-3-sulfonic acid; and sulfochlorination products of polyisocyanates or polyisocyanate mixtures based on diphenylmethane. The process according to the invention is also particularly suitable for the production of monosulfochlorides of diisocyanatotoluene where 2,4-diisocyanatotoluene or a mixture thereof with up to 35% by weight, based on the mixture as a whole, of 2,6-diisocyanatotoluene, is successively or simultaneously treated in the described manner with sulfur trioxide or chlorosulfonic acid (molar ratio (a):(b)=1:1 to 1:1.2) and with benzotrichloride (molar ratio (a):(c)=1:1.5 to 1:8) and the hydrogen chloride formed is removed from the reaction mixture in the manner described.

The process according to the invention affords the advantage over the production of sulfochlorides by the process using thionyl chloride or phosgene in conjunction with dialkyl formamide as catalyst, that the reaction mixtures formed are not difficult to separate and that no potentially carcinogenic dialkyl carbamic acid chlorides can be formed.

Another advantage lies in the fact that the aromatic trihalogen methyl compound to be used may be varied to a large extent according to its availability, the separability of the product mixture and the demand for the aromatic carboxylic acid halide simultaneously formed.

The fact that the process according to the invention can be carried out with good yields at relatively low temperatures is surprising because the sulfonation of isocyanates generally leads to extremely heat-stable dimers and, given these dimers as an intermediate stage, both the uretdione ring and also intermediately formed carbamic acid chloride have to be split again.

One particular advantage of the process according to the invention lies in the fact that, starting out from commercially produced diisocyanatotoluenes and diisocyanatodiphenyl methanes, the corresponding diisocyanatosulfochlorides may readily be obtained. These technical "TDI-sulfochlorides" or "MDI-sulfochlorides" readily obtainable by the process according to the invention are valuable starting materials for the production of polyisocyanate polyaddition products. The process products containing at least one isocyanate group and at least one sulfochloride group are highly reactive compounds which are suitable as intermediate products for a number of syntheses.

EXAMPLE 1

44 g (0.55 mole) of gaseous sulfur trioxide diluted with nitrogen are introduced at 0° to 6° C. into a solution of 66.5 g (0.5 mole) of p-tolyl isocyanate in 300 ml of 1,2-dichloroethane. The reaction product is then filtered off under suction from the dichloroethane, washed with dichloroethane and dried in an exsiccator. According to IR- and nuclear resonance spectra, the product obtained is the uretdione of p-tolyl isocyanato-o-sulfonic acid.

20 g of the sulfonation product are heated under nitrogen in 130 ml of benzotrichloride, hydrogen chloride being given off at temperatures above 100° C. The solution becomes clear at 110° C. The reaction mixture is then further heated until, at 140° C., the elimination of hydrogen chloride ceases. After the mixture of excess benzotrichloride and benzoyl chloride formed during the reaction has been distilled off, the residue is distilled at 118° C. to 123° C./0.1 Torr. 16.1 g of 1-isocyanato-2-chlorosulfonyl-4-methyl benzene are obtained.

M.p.: 36° to 38.5° C.

EXAMPLE 2

Following the procedure of Example 1, 38.4 g (0.25 mole) of 4-chlorophenyl isocyanate are sulfonated with 20 g of sulfur trioxide in 350 ml of 1,2-dichloroethane and 40 g of the sulfonation product are converted into the sulfochloride by reaction with 350 ml of benzotrichloride. 32 g of a liquid distilling at 123° to 127° C./0.3 Torr are obtained. This liquid solidifies in crystalline form on cooling.

M.p.: 38° to 42° C.

According to the IR- and NR-spectra, the product obtained is 1-isocyanato-2-chlorosulfonyl-4-chlorobenzene. Sulfur content: calculated 12.7%, observed 12.8%
Chlorine content: calculated 28.2%, observed 28.3%

EXAMPLE 3

Following the procedure of Example 1, 46.8 g (0.25 mole) of 4-trifluoromethyl phenyl isocyanate are sulfonated with 20 g of sulfur trioxide in 350 ml of 1,2-dichloroethane. The still moist reaction product is converted into the sulfochloride by reaction with 350 ml of benzotrichloride. After two distillations, 25 g of a colorless liquid boiling at 93° to 97° C./0.1 Torr are obtained. The product is uniform according to analysis by gas chromatography and, on the basis of IR-, NR- and mass spectra, is 1-isocyanato-2-chlorosulfonyl-4-trifluoromethyl benzene.

EXAMPLE 4

Following the procedure of Example 1, 870 g (5.0 moles) of commercial tolylene diisocyanate (80% of 2,4-, 20% of 2,6-isomer) are sulfonated with 400 g of sulfur trioxide in 2.4 liters of 1,2-dichloroethane. The still moist reaction product is converted into the sulfochloride by reaction with 2.5 kg of benzotrichloride at 82° to 130° C. On completion of the reaction and after benzotrichloride and benzoyl chloride have been distilled off, the crude sulfochloride may be directly distilled without further purification. 1000 g of a mixture of 2,4-diisocyanatotoluene-5-sulfochloride and 2,6-diisocyanatotoluene-5-sulfochloride are obtained.

EXAMPLE 5

Following the procedure of Example 1, 750 g (3.0 moles) of 4,4'-diisocyanatodiphenyl methane are partially sulfonated with 52 g of sulfur trioxide in 750 g of 1,2-dichloroethane. The reaction product precipitated is filtered off under suction and 30 g thereof—still moist—are converted into the sulfochloride by reaction with 300 ml of benzotrichloride at 100° to 150° C. Most of the product passes into solution. For working up, the insoluble residue is isolated by filtration and excess benzotrichloride and benzoyl chloride are completely distilled off.

A solid, non-distillable crude sulfochloride of 4,4'-diisocyanatodiphenyl methane is obtained.

Sulfur content: calculated 9.2%, observed 9.0%
Chlorine content: calculated 10.2%, observed 8.9%

EXAMPLE 6

The procedure is as in Example 1, except that, before sulfonation, the p-tolyl isocyanate used is converted into the carbamic acid chloride by the introduction of hydrogen chloride at 2° to 3° C. The suspension formed is then sulfonated. The result corresponds to that of Example 1.

EXAMPLE 7

40 g (1.1 moles) of hydrogen chloride (formation of the bis-carbamic acid chloride) and 40 g (0.5 mole) of sulfur trioxide are successively introduced at 0° to 10° C. into a solution of 125 g (0.5 mole) of 4,4'-diisocyanatodiphenyl methane in 700 ml of 1,2-dichloroethane. The suspension is then heated slowly to the boiling point of the dichloroethane, hydrogen chloride being evolved vigorously beyond about 50° C. The dichloroethane is largely distilled off and 350 ml of benzotrichloride are added to the residue. The temperature is then increased slowly to 130° C. with continued evolution of hydrogen chloride until no more gas is given off.

The reaction solution is filtered off from the insoluble residue while still hot and excess benzotrichloride and benzoyl chloride are distilled off in vacuo. According to the mass spectrum and to thin layer chromatography of the reaction product with dimethyl amine, the predominantly crystalline residue is a mixture of virtually unchanged 4,4'-diisocyanatodiphenyl methane and its mono- and disulfochloride.

What is claimed is:

1. A process for the production of an aromatic isocyanate containing aromatically bound sulfochloride groups, comprising:
   (I) reacting
      (a) an isocyanate or carbamic acid chloride which contains at least one aromatically bound isocyanate group and/or at least one aromatically bound carbamic acid chloride group, successively or simultaneously at 0° to 170° C. with
      (b) a sulfonating agent and
      (c) an organic compound containing at least one aromatically bound trihalo methyl group and
   (II) removing hydrogen chloride from the reaction mixture at 20° to 170° C.

2. The process of claim 1, wherein said isocyanate of carbamic acid chloride is selected from the group consisting of phenyl isocyanate; p-tolyl isocyanate; m-tolyl isocyanate; p-chlorophenyl isocyanate; m-chlorophenyl isocyanate; p-bromophenyl isocyanate; p-methoxy phenyl isocyanate; p-ethoxy phenyl isocyanate; p-trifluoromethyl phenyl isocyanate; m-trifluoromethyl phenyl isocyanate; 2,4-diisocyanatotoluene and its commercial mixtures with 2,6-diisocyanatotoluene; 4,4'-diisocyanatodiphenyl methane and its commercial mixtures with 2,2'-diisocyanatodiphenyl methane; 2,4'-diisocyanatodiphenyl methane and/or higher than difunctional polyisocyanates of the diphenyl methane series or the carbamic acid chlorides corresponding to these isocyanates.

3. The process of claim 1, wherein said sulfonating agent is selected from the group consisting of sulfur trioxide and chlorosulfonic acid.

4. The process of claim 1, wherein said organic compound containing at least one aromatically bound trihalo methyl group is selected from the group consisting of benzotrichloride and benzotribromide, optionally containing inert substituents.

5. The process of claim 1, wherein from 0.2 to 2.0 moles of said sulfonating agent and from 0.2 to 20 moles of said organic compound containing at least one aromatically bound trihalo methyl group are used for each mole of isocyanate or carbamic acid chloride.

* * * * *